United States Patent
Underhill et al.

(10) Patent No.: US 6,726,668 B2
(45) Date of Patent: Apr. 27, 2004

(54) DISPOSABLE ABSORBENT ARTICLE

(75) Inventors: Richard L. Underhill, Neenah, WI (US); Marsha M. Malone, Anaheim Hills, CA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 144 days.

(21) Appl. No.: 10/016,892

(22) Filed: Dec. 14, 2001

(65) Prior Publication Data

US 2003/0114816 A1 Jun. 19, 2003

(51) Int. Cl.$^7$ .................................................. A61F 13/15
(52) U.S. Cl. ..................... 604/385.101; 604/385.01; 604/378; 604/383
(58) Field of Search ................. 604/385.01, 378, 604/385.101, 379, 380, 383; 428/131–140, 170–172

(56) References Cited

U.S. PATENT DOCUMENTS

| | | | |
|---|---|---|---|
| 2,043,325 A | * 6/1936 | Jackson, Jr. ................. | 128/284 |
| 3,769,978 A | 11/1973 | DeNight et al. | |
| 3,888,257 A | 6/1975 | Cook et al. | |
| 4,041,950 A | 8/1977 | Jones, Sr. | |
| 4,285,342 A | 8/1981 | Mesek | |
| 4,324,247 A | 4/1982 | Aziz | |
| 4,381,783 A | 5/1983 | Elias | |
| 4,461,621 A | 7/1984 | Karami et al. | |
| 4,531,945 A | 7/1985 | Allison | |
| 4,906,243 A | 3/1990 | Dravland | |
| 4,988,345 A | * 1/1991 | Reising ........................ | 604/368 |
| 5,062,839 A | 11/1991 | Anderson | |
| 5,171,236 A | * 12/1992 | Dreier et al. ................. | 604/369 |
| 5,342,343 A | 8/1994 | Kitaoka et al. | |
| 5,370,632 A | 12/1994 | Beplate | |
| 5,451,442 A | 9/1995 | Pieniak et al. | |
| 5,476,458 A | 12/1995 | Glaug et al. | |
| 5,649,914 A | 7/1997 | Glaug et al. | |
| 5,658,268 A | 8/1997 | Johns et al. | |
| 5,681,298 A | 10/1997 | Brunner et al. | |
| 5,702,376 A | 12/1997 | Glaug et al. | |
| 5,702,377 A | 12/1997 | Collier, IV et al. | |
| 5,797,892 A | 8/1998 | Glaug et al. | |
| 5,885,264 A | 3/1999 | Matsushita | |
| 5,904,674 A | 5/1999 | Bonjour | |
| 5,921,974 A | 7/1999 | Kikuchi | |

(List continued on next page.)

FOREIGN PATENT DOCUMENTS

| | | |
|---|---|---|
| DE | 196 40 451 A1 | 4/1998 |
| EP | 0 217 666 A2 | 4/1987 |
| EP | 0 455 607 A1 | 11/1991 |
| FR | 2 044 554 | 5/1969 |
| WO | WO 00/09056 A1 | 2/2000 |

OTHER PUBLICATIONS

International Search Report in PCT/US 02/20729 dated Oct. 16, 2002.

Primary Examiner—Weilun Lo
Assistant Examiner—Jacqueline F Stephens (57) ABSTRACT

A disposable absorbent article for personal wear has a generally liquid permeable liner adapted for contiguity with the wearer's skin, and an outer cover. An absorbent body lies between the liner and the outer cover for absorbing liquid body waste. A surge layer lies between the liner and the absorbent body for receiving liquid body waste penetrating the liner and for subsequently releasing liquid body waste to the absorbent body. The surge layer has an inner surface, an outer surface generally facing the absorbent body and an opening extending from its inner surface toward its outer surface. A flow control layer between the liner and the absorbent body at least retards the flow of liquid body waste from the surge layer opening to the absorbent body to facilitate a prolonged feeling of wetness against the wearer's skin upon the release of liquid body waste into the article.

26 Claims, 4 Drawing Sheets

U.S. PATENT DOCUMENTS

| | | | |
|---|---|---|---|
| 5,961,505 A * | 10/1999 | Coe et al. ............... 604/378 |
| 6,162,961 A | 12/2000 | Tanner et al. |
| 6,169,225 B1 | 1/2001 | Otsubo |
| 6,235,966 B1 | 5/2001 | Magnusson et al. |
| 6,245,962 B1 | 6/2001 | Muhs et al. |
| 6,627,786 B2 | 9/2003 | Roe et al. |

* cited by examiner

DISPOSABLE ABSORBENT ARTICLE

BACKGROUND OF THE INVENTION

The present invention relates to disposable absorbent articles, such as those used as personal care products, and more particularly to such a disposable absorbent article which provides an indication of wetness to the wearer upon the release of liquid body waste into the article.

Disposable absorbent articles find widespread use as personal care products such as diapers, children's toilet training pants and other infant and child care products, adult incontinence garments and other adult care products, sanitary napkins and other feminine care products and the like, as well as surgical bandages and sponges. These articles absorb and contain body waste and are intended to be discarded after a limited period of use; i.e., the articles are not intended to be laundered or otherwise restored for reuse. Conventional disposable absorbent articles comprise an absorbent body disposed between an inner layer adapted for contacting the wearer's skin and an outer layer for inhibiting liquid waste absorbed by the absorbent body from leaking out of the article. The inner layer of the absorbent article is typically liquid permeable to permit body waste to pass therethrough for absorption by the absorbent body.

For example, children's toilet training pants serve as a training aid as a child transitions from diapers to underpants. Conventional toilet training pants are three-dimensional articles, similar to underpants in appearance, but constructed with a liquid permeable inner layer and an absorbent body to provide the absorbent function of disposable absorbent articles. An initial step in the toilet training process is for the child to recognize when urination occurs. However, where the training pants quickly and effectively draw urine away from the skin and retain the urine in the absorbent body, the inner layer of the pants remains dry and comfortable against the child's skin. As a result, there is little or no recognizable indication to the child that he or she has urinated. To this end, it is desirable to provide some indication to the child that the child has urinated in the training pants.

Therefore, despite advancements in the construction of disposable absorbent articles, there continues to be a need for relatively easily constructed disposable absorbent articles capable of indicating to the wearer that a release of liquid body waste has occurred.

SUMMARY OF THE INVENTION

In general, a disposable absorbent article of the present invention comprises a generally liquid permeable liner adapted for contiguity with the wearer's skin, and an outer cover. An absorbent body lies between the liner and the outer cover for absorbing liquid body waste. A surge layer lies between the liner and the absorbent body for receiving liquid body waste penetrating the liner and for subsequently releasing liquid body waste to the absorbent body. The surge layer has an inner surface generally facing the liner and an outer surface generally facing the absorbent body, and has an opening therein extending from the inner surface of the surge layer toward its outer surface. A flow control layer between the liner and the absorbent body at least retards the flow of liquid body waste from the surge layer opening to the absorbent body.

In another embodiment, toilet training pants of the present invention comprise an anterior region, a posterior region and a crotch region disposed longitudinally therebetween. The anterior region, posterior region and crotch region are integrally formed and configured to define a central waist opening and a pair of leg openings of said pants, with the crotch region extending generally laterally between said leg openings. A generally liquid permeable liner extends from the anterior region through the crotch region to the posterior region of the pants and is adapted for contiguity with the wearer's skin. An absorbent body lies between the liner and an outer cover for absorbing liquid body waste. A surge layer lies between the liner and the absorbent body for receiving liquid body waste penetrating the liner and for subsequently releasing liquid body waste to the absorbent body. The surge layer has an inner surface generally facing the liner and an outer surface generally facing the absorbent body, and has an opening therein extending from the inner surface of the surge layer toward its outer surface. A flow control layer between the liner and the absorbent body at least retards the flow of liquid body waste from the surge layer opening to the absorbent body.

A method of the present invention for manufacturing toilet training pants generally comprises forming an opening in a surge layer to extend from an inner surface of the surge layer toward an outer surface thereof. A flow control layer is positioned adjacent the surge layer generally at the surge layer opening for at least retarding the flow of liquid body waste from said opening. The surge layer and flow control layer are positioned between a liner and an absorbent body adapted for absorbing liquid body waste, with the liner being adapted for contiguity with the wearer's skin and being generally liquid permeable. The surge layer, the flow control layer and the absorbent body are positioned generally between the liner and the absorbent body, with the liner and outer cover together defining an anterior region, a crotch region and a posterior region of the training pants. The training pants are configured such that the anterior region, crotch region and posterior region generally form a central waist opening and a pair of leg openings of the training pants with the crotch region being disposed between the leg openings Other aspects and features of this invention will be in part apparent and in part pointed out hereinafter.

BRIEF DESCRIPTION OF THE DRAWINGS

Corresponding reference characters indicate corresponding parts throughout the drawings.

DEFINITIONS

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

(c) "Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, and fibers having contact angles greater than 90 are designated "non-wettable" or hydrophobic.

(d) "Layer" when used in the singular can have the dual meaning of a single element or a plurality of elements.

(e) "Liquid impermeable" when used in describing a layer or multi-layer laminate means that liquid body waste, such as urine, will not pass through the layer or laminate, under ordinary use conditions, in a direction generally perpendicular to the plane of the layer or laminate at the point of liquid contact.

(f) "Liquid permeable" refers to any material that is not liquid impermeable.

(g) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

(h) "Non-woven" and "non-woven web" refer to materials and webs of material which are formed without the aid of a textile weaving or knitting process.

(i) "Pliable" refers to materials which are compliant and which will readily conform to the general shape and contours of the wearer's body.

(j) "Spunbond" refers to small diameter fibers which are formed by extruding molten thermoplastic material as filaments from a plurality of fine capillaries of a spinnerette having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, more particularly, between about 0.6 and about 10.

(k) "Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

(l) "Surface" includes any layer, film, woven, non-woven, laminate, composite, or the like, whether permeable or impermeable to air, gas, and/or liquids.

(m) "Thermoplastic" describes a material which softens when exposed to heat and which substantially returns to a non-softened condition when cooled to room temperature.

(n) "Three dimensional" refers to a garment similar to underwear, shorts or pants in that it has continuous leg and waist openings that are bounded by material of which the garment is made. The garment may or may not have manually tearable seams.

DETAILED DESCRIPTION OF THE PREFERRED EMBODIMENTS

Figure 1:
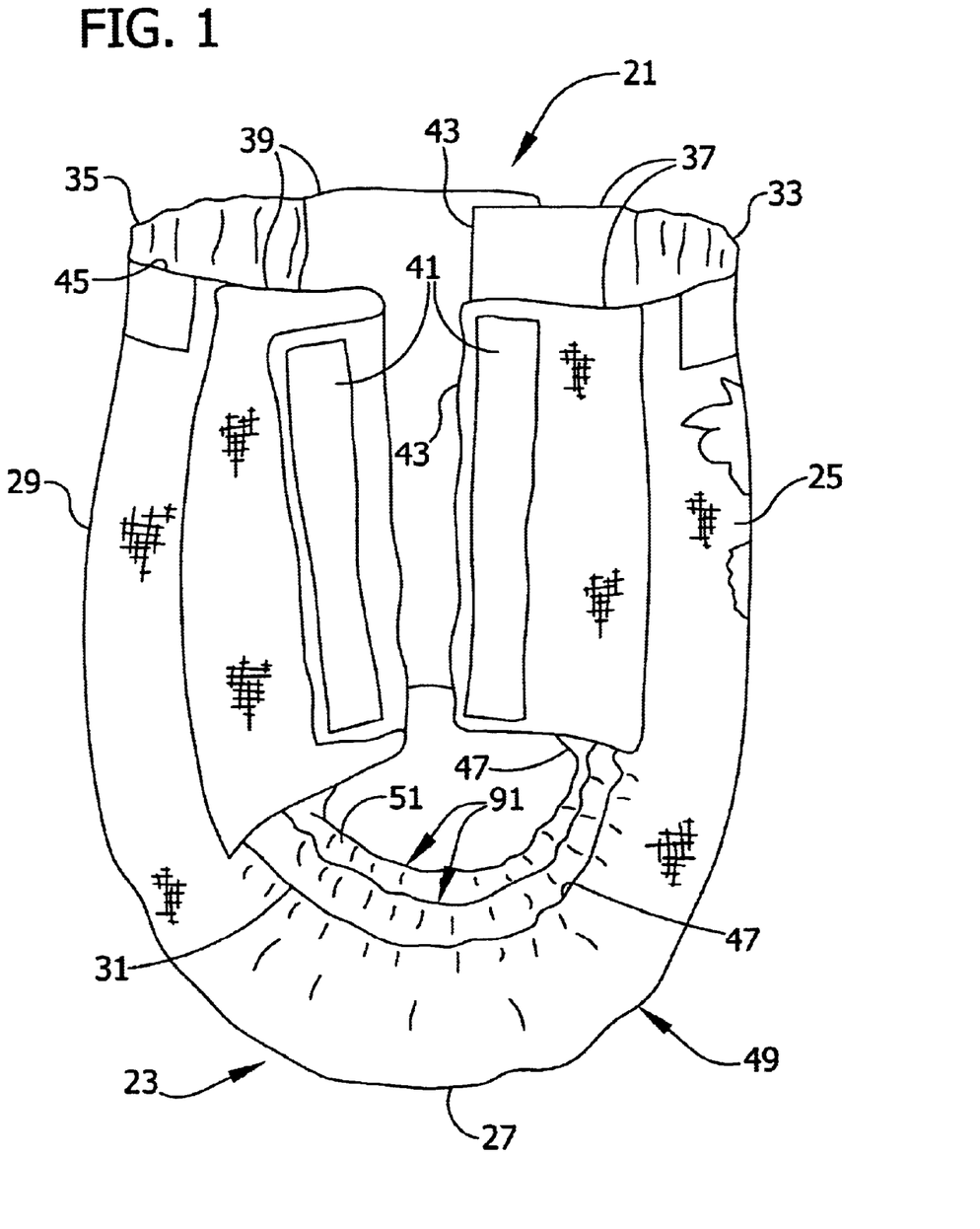
FIG. 1 is a side perspective of children's toilet training pants of the present invention.

Referring now to the drawings and in particular to FIG. 1, a disposable absorbent article of the present invention is shown in the form of children's toilet training pants and is indicated in its entirety by the reference numeral 21. As used herein, a disposable absorbent article refers to an article which may be placed against or in proximity to the body (i.e., contiguous to the body) of the wearer to absorb and contain various liquid waste discharged from the body. Such articles are intended to be discarded after a limited period of use instead of being laundered or otherwise restored for reuse. It is understood that the present invention is applicable to various other disposable absorbent articles, such as diapers and other infant and child care products, adult incontinence garments and other adult care products, sanitary napkins and other feminine care products and the like, as well as surgical bandages and sponges, without departing from the scope of the present invention.

By way of illustration only, various materials and methods for constructing training pants 21 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 2:
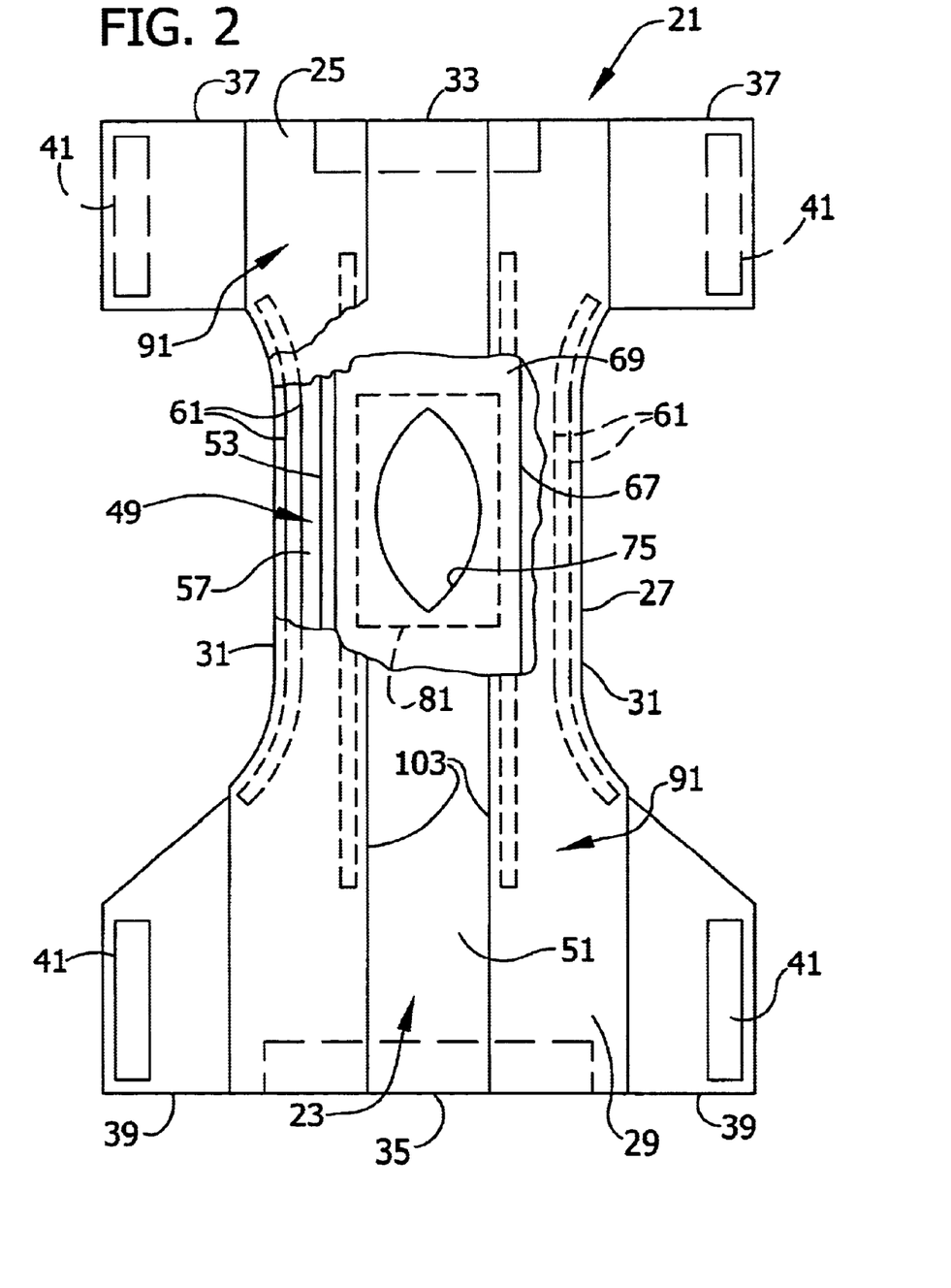
FIG. 2 is a top plan of the training pants of FIG. 1 with the pants shown unfastened and laid flat and portions of the pants broken away to reveal internal construction thereof.

The training pants 21 of the illustrated embodiment generally comprise a central absorbent assembly 23 extending longitudinally from an anterior region 25 of the training pants through a crotch region 27 to a posterior region 29 of the training pants. As illustrated in FIG. 2, the central absorbent assembly 23 is generally rectangular and has laterally opposite side edges 31 and longitudinally opposite front and rear waist edges, respectively designated 33 and 35. Front and rear side panels 37, 39, respectively, are secured to the central absorbent assembly 23 as will be described later herein and extend laterally outward therefrom respectively at the anterior and posterior regions 25, 29 of the training pants 21.

To form the three-dimensional training pants 21, corresponding front and rear side panels 37, 39 (e.g., the front left side panel and the rear left side panel) are refastenably secured together, using fastening assemblies 41, along generally vertical seams 43. Alternatively, the front and rear side panels 37, 39 may be permanently secured together, such as by ultrasonic bonding, or they may be formed integrally with each other and with the central absorbent assembly 23. Securing the side panels 37, 39 together provides a central waist opening 45 and a pair of laterally spaced leg openings 47 of the training pants 21. The training pants 21 are worn by inserting the wearer's feet through the waist opening 45 and the respective leg openings 47; grasping the training pants near the waist opening; and then pulling the pants up along the wearer's legs until the crotch region 27 of the training pants fits snugly against the crotch of the wearer.

Figure 3:
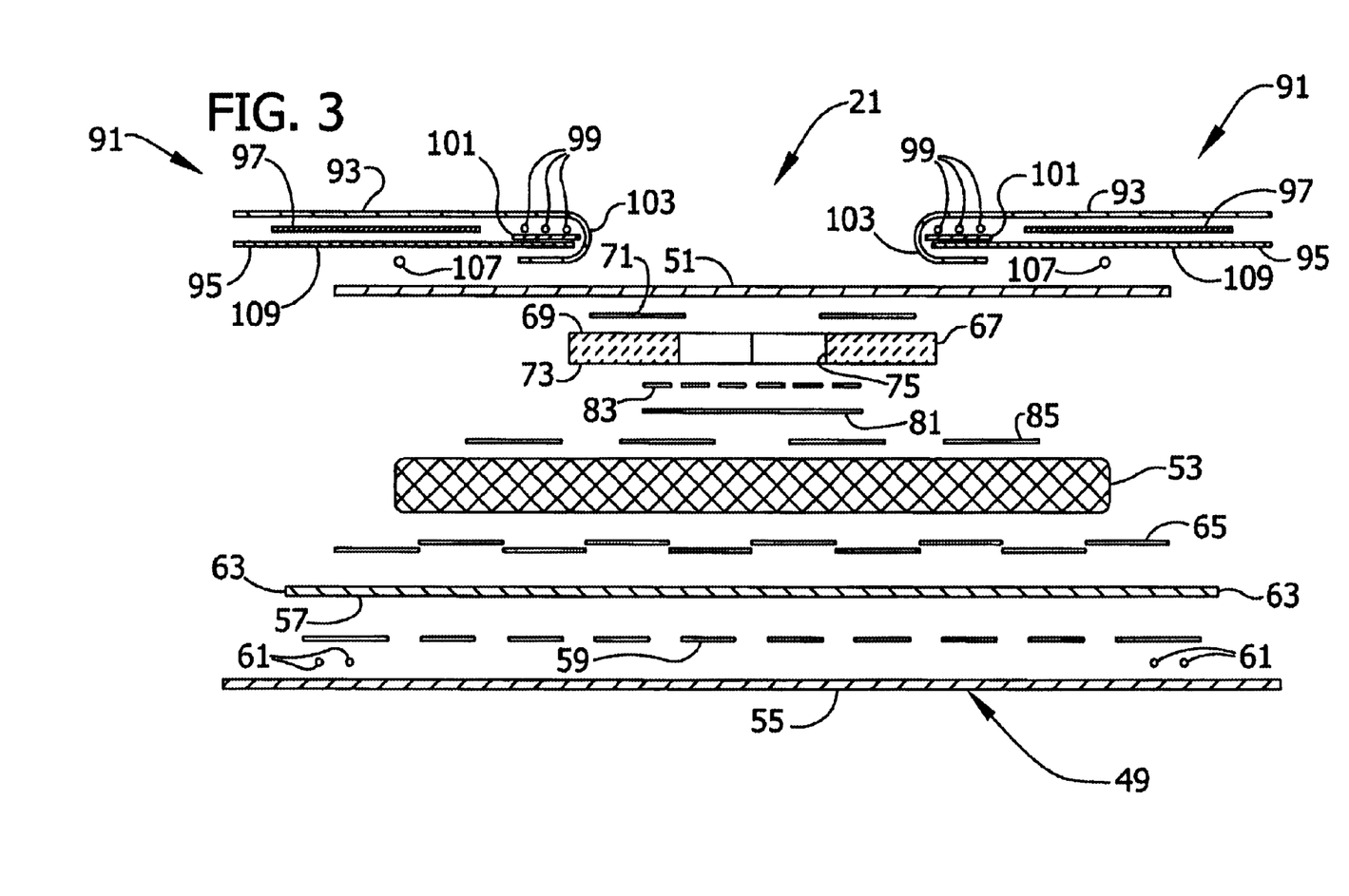
FIG. 3 is a schematic, separated cross-section of the training pants of FIG. 1 taken transversely through a crotch region of the pants.

With reference to FIG. 3, the central absorbent assembly 23 of the training pants 21 comprises an outer cover, generally indicated at 49, a bodyside liner 51 and an absorbent body 53 disposed between the outer cover and the liner. The outer cover 49 can be elastic, stretchable or non-stretchable and is desirably a multi-layered laminate structure of which at least one of the layers is liquid impermeable. For example, the outer cover 49 of the illustrated embodiment is of two-layer construction, including an outer layer 55 constructed of a liquid permeable material and an inner layer 57 constructed of a liquid impermeable material joined together by a laminate adhesive 59. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. It is understood that the outer cover 49 may instead be constructed of a single layer of impermeable material without departing from the scope of this invention.

The liquid permeable outer layer 55 of the outer cover 49 can be any suitable material and is desirably one that provides a generally cloth-like texture. One example of such a material is a 20 gsm (grams per square meter) spunbond polypropylene non-woven web. The outer layer 55 may also be constructed of the same materials from which the bodyside liner 51 is constructed as described later herein. Also, while it is not a necessity for the outer layer 55 of the outer cover 49 to be liquid permeable, it is desired that it provide a relatively cloth-like texture to the wearer.

The liquid impermeable inner layer 57 of the outer cover 49 can be either vapor permeable (i.e., "breathable") or vapor impermeable. The inner layer 57 is desirably manufactured from a thin plastic film, although other flexible liquid impermeable materials may also be used. The liquid impermeable inner layer 57 (or the liquid impermeable outer cover 49 where the outer cover is of a single-layer construction) inhibits liquid body waste from leaking out of the pants and wetting articles, such as bed sheets and clothing, as well as the wearer and care giver. A suitable liquid impermeable material for such use is a 0.02 millimeter polyethylene film commercially available from Huntsman Packaging of Newport News, Va., U.S.A.

Where the outer cover 49 is of single-layer construction, it can be embossed and/or matte finished to provide a more cloth-like appearance. As earlier mentioned, the liquid impermeable layer of the outer cover 49 can permit vapors to escape from the pants 21 while preventing liquids from passing therethrough. A suitable liquid impermeable, vapor permeable material is composed of a microporous polymer film or a non-woven fabric which has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

Leg elastic members 61 are secured between the outer and inner layers 55, 57 of the outer cover 49, such as by being bonded therebetween by the laminate adhesive 59, generally adjacent laterally outer edges 63 of the inner layer of the outer cover. Alternatively, the leg elastic members 61 may be disposed between the outer cover 49 and the bodyside liner 51, or between other layers of the pants 21. A wide variety of elastic materials may be used for the leg elastic members 61. As is well known to those skilled in the art, suitable elastic materials include sheets, strands or ribbons of natural rubber, synthetic rubber, or thermoplastic elastomeric polymers. The elastic materials can be stretched and secured to a substrate, secured to a gathered substrate, or secured to a substrate and then elasticized or shrunk, for example with the application of heat, such that elastic retractive forces are imparted to the substrate. For example, one suitable elastic material is a dry-spun coalesced multifilament spandex elastomeric thread sold under the trade name LYCRA® and available from E. I. du Pont de Nemours and Company, Wilmington, Del., U.S.A.

The absorbent body 53 is somewhat rectangular and is desirably constructed to be generally compressible, pliable, non-irritating to the wearer's skin and capable of absorbing and retaining liquid body waste, such as urine. The absorbent body 53 may be composed of hydrophillic fibers, such as a web of cellulosic fluff, mixed with particles of a high-absorbency material commonly known as superabsorbent material. More particularly, the absorbent body 53 may be composed of a matrix of wood pulp fluff and superabsorbent hydrogel-forming particles. Alternatively, the absorbent body 53 may be composed only of cellulosic pulp fluff, only of superabsorbent materials, or a combination of both and/or other absorbent or non-absorbent materials.

One suitable type of wood pulp fluff is identified with the trade designation CR1654, available from U.S. Alliance, Childersburg, Ala., U.S.A., and is a bleached, highly absorbent sulfate wood pulp containing primarily soft wood fibers. However, the wood pulp fluff can be exchanged with other hydrophillic fiber materials, such as synthetic, polymeric, or meltblown fibers or with a combination of meltblown fibers and natural fibers. Suitable superabsorbent materials can be selected from natural, synthetic, and modified natural polymers and materials. The superabsorbent materials can be inorganic materials, such as silica gels, or organic compounds, such as cross-linked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany.

The absorbent body 53 may or may not be wrapped or encompassed by a suitable wrapping (not shown) which maintains the integrity and/or shape of the absorbent body. The absorbent body 53 overlays the inner layer 57 of the outer cover 49, extending laterally between the leg elastic members 61, and is secured to the inner layer, such as by being bonded thereto with adhesive 65. However, it is understood that the absorbent body 53 may free from securement to the inner layer 57 of the outer cover 49 without departing from the scope of this invention.

A surge layer 67 lies between the bodyside liner 51 and the absorbent body 53 to help decelerate and diffuse surges or gushes of liquid body waste penetrating the liner. Desirably, the surge layer 67 can rapidly accept and temporarily hold the liquid body waste prior to slowly releasing the liquid body waste to flow toward the absorbent body. The surge layer 67 can include various types of fabrics, such as spunbond fabrics, meltblown fabrics, bonded carded webs, through-air bonded carded webs, knit fabrics, woven fabrics, airformed fabrics and the like, as well as combinations thereof. The fabrics can be composed of various types of fibers, such as polyolefin fibers, polyester fibers, bicomponent fibers, conjugate fibers, and the like, as well as combinations thereof.

For example, one suitable material from which the surge layer 67 can be constructed has a basis weight of about 50 gsm, and includes a through-air-bonded-carded web of a homogeneous blend of 60 percent 3 denier bicomponent fiber including a polyester core/polyethylene sheath, commercially available from KoSa Corporation of Salisbury, N.C., U.S.A., and 40 percent 6 denier polyester fiber, also commercially available from KoSa Corporation. Other examples of suitable surge layers 67 are described in U.S. Pat. Nos. 5,486,166; 5,490,846; 5,562,650; and 5,364,382, the entire disclosures of which are hereby incorporated by reference in a manner that is consistent herewith. The surge layer 67 desirably has a permeability in the range of about 2000–4000 darcies.

The surge layer 67 of the illustrated embodiment has an inner surface 69 generally facing the bodyside liner 51 and secured thereto, such as by being bonded thereto with a suitable adhesive 71. It is understood, though, that the surge layer 67 need not be secured to the liner 51. An outer surface 73 of the surge layer 67 generally faces the absorbent body 53. The surge layer 67 has a generally ovate opening 75 (FIGS. 2 and 3) formed therein generally at the crotch region 27 of the pants 21 and extending through the full thickness of the surge layer from its inner surface to its outer surface. However, it is contemplated that the surge layer opening 75 may be other than ovate, such as circular, square, triangular, irregular-shaped, etc., without departing from the scope of this invention. It is also contemplated that the surge layer opening 75 may extend from the inner surface 69 of the surge layer 67 toward the outer surface 73 thereof without extending through the full thickness of the surge layer. It is further contemplated that the surge layer 67 may have two or more openings formed therein. The surge layer opening 75, or collective openings, is desirably in the range of about five percent to about forty percent of the surface area of the inner surface 69 of the surge layer 67.

As an example, the surge layer 67 may be about 2.5 inches wide and have a length in the range of about ten inches to about twelve inches. The opening 75 formed in such a surge layer 67, or the openings collectively if more than opening is formed in the surge layer, may be about two inches wide and about five inches long, and more particularly may be about 1.5 inches wide and about 2.5 inches long. The cross-sectional dimensions of the surge layer opening 75 are desirably generally uniform throughout the depth of the opening. However, the cross-sectional dimensions of the opening 75 may instead gradually decrease as the opening extends from the inner surface 69 of the surge layer 67 toward the outer surface 73.

A flow control layer 81 lies between the outer surface 73 of the surge to layer 67 and the absorbent body 53, generally underlying the surge layer opening 75, to inhibit the release of urine from the opening to the absorbent body. The flow control layer 81 is desirably sized slightly larger than the surge layer opening 75, but smaller than the entire surge layer, to extend laterally beyond the peripheral edges of the opening. For example, the flow control layer 81 of the illustrated embodiment has a width of about two inches and a length of about three inches to extend at least about 0.25 inches beyond the periphery of the surge layer opening 75. The flow control layer 81 is secured to the outer surface 73 of the surge layer 67, such as by being bonded thereto with suitable adhesive 83 and is also secured to the absorbent body 53, such as by being bonded thereto with additional adhesive 85. However, it is understood that the flow control layer 81 need not be secured to absorbent body 53 and/or to the surge layer 67 to remain within the scope of this invention.

It is also understood that the flow control layer 81 may be sized smaller than the surge layer opening 75, or it may be sized equal to or larger than the surge layer to extend up to or beyond the edges of the surge layer. Also, while not shown in the drawings, it is contemplated that the flow control layer 81 may also, or may alternatively, line the side wall of the surge layer opening 75 without departing from the scope of this invention. Instead of lying between the surge layer 67 and the absorbent body 53, the flow control layer may lie between the liner and surge layer, overlaying the surge layer opening 75. In such an embodiment, the flow control layer 81 may be sufficiently sized to allow the flow control layer to sag into the surge layer opening 75 for pooling urine therein upon the release of a surge of urine by the wearer of the pants 21. The flow control layer 81 may also lie within the surge layer 67 itself, or be sandwiched between two surge layers, and remain within the scope of this invention.

The flow control layer 81 may be constructed of either an impermeable material or a permeable material, it being understood that the rate at which urine passes from the surge layer opening 75 to the absorbent body 53 is generally a function of the permeability of the flow control layer. In any event, the permeability of the flow control layer 81 is desirably less than the permeability of the surge layer 67. As an example, a suitable impermeable material from which the flow control layer 81 may be constructed is a polyolefin film that blocks the flow of urine from the surge layer opening 75 therethrough to the absorbent body 53. Urine in the surge layer opening 75 is instead directed by the flow control layer 81 to migrate laterally and/or longitudinally outward (e.g., within the surge layer 67) toward the peripheral edges of the flow control layer and then around the edges thereof to the absorbent body 53. It is contemplated that the film may also be treated, such as by being embossed or subjected to other suitable processing, to provide a textured surface over which urine flows toward the peripheral edges of the flow control layer 81. As another example, a suitable permeable material from which the flow control layer 81 may be constructed is a meltblown hydrophobic non-woven layer which retards, but does not prevent, urine in the surge layer opening 75 from penetrating through the flow control layer and flowing to the absorbent body 53.

Still referring to FIG. 3, the bodyside liner 51 overlays the absorbent body 53 to isolate the wearer's skin from liquid body waste retained by the absorbent body and is secured to at least a portion of the absorbent body, such as by being bonded thereto with adhesive 85. The liner 51 further extends beyond the absorbent body 53 to overlay a portion of the inner layer 57 of the outer cover 49, particularly in the crotch region 27 of the pants 21, and is secured thereto, such as by being bonded thereto by adhesive 65, to substantially enclose the absorbent body between the outer cover and the liner about the periphery of the absorbent body. Although the bodyside liner 51 shown in FIG. 3 is slightly narrower than the outer cover 49, it is understood that the liner and outer cover may be of the same dimensions, or the liner may be sized larger than the outer cover, without departing from the scope of this invention. It is also contemplated that the liner 51 may not extend beyond the absorbent body 53 and may not be secured to the outer cover 49 and/or to the absorbent body 53. The bodyside liner 51 is desirably compliant, soft feeling, and non-irritating to the wearer's skin and can be less hydrophilic than the absorbent body 53 to provide a relatively dry surface to the wearer and permit liquid body waste to readily penetrate through its thickness.

The bodyside liner 51 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and non-woven fabrics can be used for the bodyside liner 51. For example, the liner 51 can be composed of a meltblown or spunbonded web of polyolefin fibers. Alternatively, the liner 51 can be a bonded-carded web composed of natural and/or synthetic fibers. The bodyside liner 51 can also be composed of a substantially hydrophobic material, and the hydrophobic material can, optionally, be treated with a surfactant or otherwise processed to impart a desired level of wetability and hydrophilicity. For example, the material can be surface treated with about 0.45 weight percent of a surfactant mixture including AHCOVEL® N-62 available from Uniqema, Inc., a division of ICI of New Castle, Del., U.S.A, and GLUCOPON® 220UP available from Cognis Corporation of Ambler, Pa., U.S.A, in an active ratio of 3:1. The surfactant can be applied by any conventional means, such as spraying, printing, brush coating or the like. The surfactant can be applied to the entire liner 51 or it can be selectively applied to particular sections of the liner.

A particularly suitable bodyside liner 51 is constructed of a non-woven bicomponent web having a basis weight of about 27 gsm. The non-woven bicomponent can be a spunbonded bicomponent web, or a bonded-carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Fibers having other orientations, such as multi-lobe, side-by-side, end-to-end may be used without departing from the scope of the invention. Also, although the outer cover 49 and bodyside liner 51 of the central absorbent assembly 23 can include elastomeric materials, it is contemplated that the central absorbent assembly may instead be generally inelastic, wherein the outer cover, the bodyside liner and the absorbent body 53 are composed of materials which are generally non-elastomeric.

The front and rear side panels 37, 39 of the training pants 21 are bonded to the central absorbent assembly 23 at the respective anterior and posterior regions 25, 29 of the pants and extend outward beyond the laterally opposite edges 31 of the assembly. For example, the front side panels 37 of the illustrated embodiment are secured to the inner layer 57 of the outer cover 49, such as by being bonded thereto by adhesive (not shown), by thermal bonding or by ultrasonic bonding. These side panels 37 may also be secured to the outer layer 55 of the outer cover 49, such as by being bonded thereto by adhesive (not shown), by thermal bonding or by ultrasonic bonding. The rear side panels 39 are secured to the outer and inner layers 55, 57 of the outer cover 49, at the posterior region 29 of the training pants 21, in substantially the same manner as the front side panels 37. Alternatively, the side panels 37, 39 may be formed integrally with the central absorbent assembly 23, such as by being formed integrally with the outer cover 49, the bodyside liner 51 or other layers of the pants 21.

For improved fit and appearance, the side panels 37, 39 desirably have an average length measured parallel to the longitudinal axis of the training pants 21 that is about 20 percent or greater, and more desirably about 25 percent or greater, of the overall length of the training pants, also measured parallel to the longitudinal axis. For example, for training pants 21 having an overall length of about 54 centimeters, the side panels 37, 39 desirably have an average length of about 10 centimeters or greater, and more desirably an average length of about 15 centimeters. Each of the side panels 37, 39 can be constructed of one or more individual, distinct pieces of material. For example, each side panel 37, 39 can include first and second side panel portions (not shown) joined at a seam (not shown), with at least one of the portions including an elastomeric material. Alternatively, each individual side panel 37, 39 can be constructed of a single piece of material folded over upon itself along an intermediate fold line (not shown).

The side panels 37, 39 desirably include an elastic material capable of stretching laterally. Suitable elastic materials, as well as one described process for incorporating elastic side panels 37, 39 into training pants 21, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panels 37, 39 may include other woven or non-woven materials, such as those described above as being suitable for the outer cover 49 or bodyside liner 51, or stretchable but inelastic materials.

Containment flaps, generally indicated at 91, are secured to the body side liner 51 in generally parallel, spaced relation with each other laterally inward of the leg openings 47 to provide a barrier against the flow of urine to the leg openings. The containment flaps 91 extend longitudinally from the anterior region 25 of the training pants 21, through the crotch region 27 to the posterior region 29 of the pants. Each containment flap 91 comprises a non-woven layer 93 and a film layer 95 secured to the non-woven layer, such as by being bonded thereto by adhesive 97. Flap elastics 99 are secured by suitable adhesive 101 between the non-woven layer 93 and the film layer 95 generally at a distal end 103 of the flap 91, with the non-woven layer 93 being folded over the flap elastics 99 and the film layer 95 at the distal end 103. The flap 91 is secured to the bodyside liner 51 by a seam of adhesive 107 to define a proximal end 109 of the flap.

The flap elastics 99 of the illustrated embodiment comprise three individual strands of elastomeric material extending longitudinally along the distal end 103 of the flap 91 in generally parallel, spaced relation with each other. One suitable elastic strand is a LYCRA® T151 940 decitex elastic which can be obtained from E. I. du Pont de Nemours Co. of Wilmington, Del. The elastic strands are secured between the non-woven layer 93 and the film layer 95 while in an elastically contractible condition such that contraction of the strands gathers and shortens the distal end 103 of the containment flap 91. As a result, the elastic strands bias the distal end 103 of each flap 91 toward a position spaced from the proximal end 109 of the flap so that the flap extends away from the liner 51 in a generally upright orientation of the flap, especially in the crotch region 27 of the training pants 21, when the pants are fitted on the wearer. It is understood, however, that the containment flaps 91 may be omitted from the training pants 21 without departing from the scope of the invention.

Figure 4:
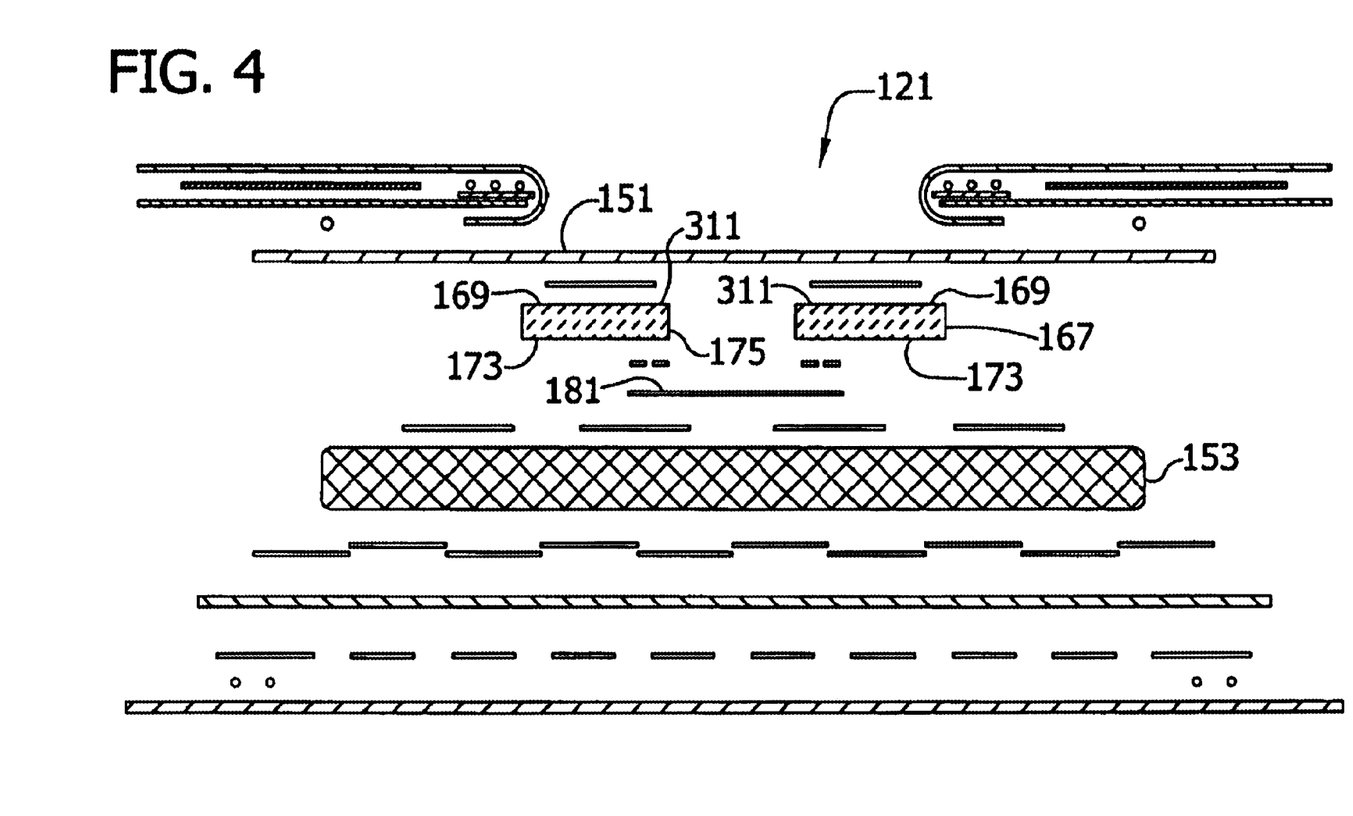
FIG. 4 is a schematic, separated cross-section taken transversely through a crotch region of children's toilet training pants of a second embodiment of the present invention.

FIG. 4 illustrates a second embodiment of training pants 121 similar to the training pants 21 of the first embodiment including a surge layer 167 having an opening 175 therein extending from an inner surface 169 of the surge layer through the full thickness thereof to an outer surface 173 of the surge layer, and a flow control layer 181 for inhibiting the flow of urine from the surge layer opening to the absorbent body 153. The surge layer 167 of this second embodiment is constructed of a pair of surge layer elements 311 spaced laterally from each other along the full length of the surge layer, with the spacing between the surge layer elements defining the surge layer opening 175. For example, the two surge layer elements 311 of the illustrated embodiment are spaced laterally from each other by a distance of about 0.5 inches to about 1.5 inches, and more desirably about 0.75 inches. The flow control layer 181 underlying the surge layer opening 175 is sized to extend laterally beyond the periphery of the opening by at least about 0.25 inches.

In use, when the wearer of the training pants 21, 121 urinates therein, urine penetrates the liner 51, 151 for flow to the inner surface 69, 169 of the surge layer 67, 167, and more particularly to the opening 75, 175 formed in the surge layer. When the initial surge of urine impacts the flow control layer 81, 181, urine can back-splash through the liner 51, 151 to contact the wearer's skin. The flow control layer 81, 181 also retards the flow of urine through the surge layer opening 75, 175 to the absorbent body 53, 153, resulting in pooling of urine in the surge layer opening. This pooling facilitates the flow back of urine through the liner 51, 151 to provide a prolonged (as compared to conventional training pants) feeling of wetness against the wearer's skin for indicating that the wearer has urinated in the pants. Eventually, urine in the surge layer opening 75, 175 flows therefrom around (e.g., where the flow control layer 81, 181 is constructed of an impermeable material) and/or through (e.g., where the flow control layer is constructed of a permeable material) the flow control layer to the absorbent body 53, 153 for absorption thereby to again provide a dry, comfortable feeling to the wearer.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A disposable absorbent article for personal wear, said disposable absorbent article comprising:
   a generally liquid permeable liner adapted for contiguity with the wearer's skin;
   an outer cover;
   an absorbent body between the liner and the outer cover for absorbing liquid body waste;
   a surge layer between the liner and the absorbent body for receiving liquid body waste penetrating the liner and for subsequently releasing said liquid body waste to the absorbent body, the surge layer having an inner surface generally facing the liner and an outer surface generally facing the absorbent body, said surge layer having an opening therein extending from the inner surface of said surge layer toward its outer surface; and
   a flow control layer between the liner and the absorbent body for at least retarding the release of liquid body waste from the surge layer opening to the absorbent body.

2. A disposable absorbent article as set forth in claim 1, wherein the flow control layer is permeable.

3. A disposable absorbent article as set forth in claim 1 wherein the flow control layer is impermeable.

4. A disposable absorbent article as set forth in claim 3 wherein the flow control layer is constructed of a film.

5. A disposable absorbent article as set forth in claim 4 wherein the flow control layer is constructed of a polyethylene film.

6. A disposable absorbent article as set forth in claim 3 wherein the flow control layer is textured.

7. A disposable absorbent article as set forth in claim 1 wherein the surge layer opening has a length of less than or equal to about 5 inches and a width of less than or equal to about 2 inches at the inner surface of the surge layer.

8. A disposable absorbent article as set forth in claim 1 wherein the surge layer opening has a length of about 2.5 inches and a width of about 1.5 inches at the inner surface of the surge layer.

9. A disposable absorbent article as set forth in claim 1 wherein the surge layer opening extends entirely through the surge layer from its inner surface to its outer surface.

10. A disposable absorbent article as set forth in claim 9 wherein the surge layer opening has a generally uniform cross-section as the opening extends from the inner surface of the surge layer toward its outer surface.

11. A disposable absorbent article as set forth in claim 9 wherein the surge layer comprises a pair of surge layer elements spaced laterally from each other along the length of the surge layer to define said surge layer opening.

12. A disposable absorbent article as set forth in claim 11 wherein the surge layer elements are spaced laterally from each other by a distance of about 0.5 inches to about 2.5 inches.

13. A disposable absorbent article as set forth in claim 1 wherein the flow control layer is larger than the surge layer opening and is arranged relative thereto to extend outward beyond the periphery of said opening.

14. A disposable absorbent article as set forth in claim 13 wherein the surge layer opening is generally ovate.

15. A disposable absorbent article as set forth in claim 14 wherein the surge layer opening has a length of about 2.5 inches and a width of about 1.5 inches, the flow control layer having a length of about 3.0 inches and a width of about 2.0 inches and being arranged relative to the surge layer to extend at least about 0.25 inches outward beyond the periphery of said surge layer opening.

16. A disposable absorbent article as set forth in claim 1 wherein the flow control layer is disposed between the absorbent body and the outer surface of the surge layer and generally underlies the surge layer opening.

17. Toilet training pants comprising:
   an anterior region, a posterior region and a crotch region disposed longitudinally therebetween, said anterior region, posterior region and crotch region being integrally formed and configured to define a central waist opening and a pair of leg openings of said pants, the crotch region extending generally laterally between said leg openings;

a generally liquid permeable liner extending from the anterior region through the crotch region to the posterior region of said pants and being adapted for contiguity with the wearer's skin;

an outer cover;

an absorbent body between the liner and the outer cover for absorbing liquid body waste;

a surge layer between the liner and the absorbent body for receiving liquid body waste penetrating the liner and for subsequently releasing said liquid body waste to the absorbent body, the surge layer having an inner surface generally facing the liner and an outer surface generally facing the absorbent body, said surge layer having an opening therein extending from the inner surface of said surge layer toward its outer surface; and a flow control layer between the liner and the absorbent body for at least retarding the flow of liquid body waste from the surge layer opening to the absorbent body.

18. Toilet training pants as set forth in claim 17 wherein the flow control layer is disposed between the absorbent body and the outer surface of the surge layer and generally underlies the surge layer opening.

19. Toilet training pants as set forth in claim 17 wherein the surge layer opening extends entirely through the surge layer from its inner surface to its outer surface.

20. Toilet training pants as set forth in claim 17 wherein the surge layer opening has a generally uniform cross-section as the opening extends from the inner surface of the surge layer toward its outer surface.

21. Toilet training pants as set forth in claim 17 wherein the surge layer opening is generally in the crotch region of the training pants.

22. A method of manufacturing toilet training pants comprising: forming an opening in a surge layer to extend from an inner surface of said surge layer toward an outer surface thereof;

positioning a flow control layer adjacent the surge layer generally at said surge layer opening for at least retarding the flow of liquid body waste from said opening;

positioning the surge layer and the flow control layer between a liner and an absorbent body adapted for absorbing liquid body waste, the liner being adapted for contiguity with the wearer's skin and being generally liquid permeable;

positioning the surge layer, the flow control layer and the absorbent body generally between said liner and said outer cover, said liner and outer cover together defining an anterior region, a crotch region and a posterior region of said training pants; and configuring the braining pants such that the anterior region, crotch region and posterior region generally form a central waist opening and a pair of leg openings of the training pants with the crotch region being disposed between the leg openings.

23. A method as set forth in claim 22 further comprising positioning the flow control layer adjacent to an outer surface of the surge layer generally at the surge layer opening such that said flow control layer lies between said surge layer and said absorbent body with said flow control layer generally underlying said surge layer opening.

24. A method as set forth in claim 23 further comprising positioning the flow control layer adjacent said outer surface of the surge layer such that said flow control layer extends outward beyond the periphery of the surge layer opening.

25. A method as set forth in claim 22 wherein said step of forming an opening in the surge layer comprises laterally spacing a pair of surge layer elements along the length of the surge layer to define said surge layer opening.

26. A disposable absorbent article as set forth in claim 1 further comprising an anterior region, a posterior region and a crotch region disposed longitudinally therebetween, said anterior region, posterior region and crotch region being integrally formed and wherein the surge layer opening is disposed longitudinally generally in the crotch region of the disposable absorbent article.

* * * * *

UNITED STATES PATENT AND TRADEMARK OFFICE
CERTIFICATE OF CORRECTION

PATENT NO. : 6,726,668 B2
DATED : April 27, 2004
INVENTOR(S) : Underhill et al.

It is certified that error appears in the above-identified patent and that said Letters Patent is hereby corrected as shown below:

Column 2,
Line 38, "openings" should read -- openings. --.

Column 4,
Line 46, "et al;" should read -- et al.; --.

Column 7,
Line 46, "more than opening" should read -- more than one opening --.

Column 10,
Line 42, "body side" should read -- bodyside --.

Column 12,
Line 14, "claim 1," should read -- claim 1 --.
Line 46, "2.5" should read -- 1.5 --.

Column 14,
Line 15, "braining" should read -- training --.

Signed and Sealed this

First Day of February, 2005

JON W. DUDAS
*Director of the United States Patent and Trademark Office*